US006712793B1

(12) United States Patent
Geiger et al.

(10) Patent No.: US 6,712,793 B1
(45) Date of Patent: Mar. 30, 2004

(54) NEEDLE GUARD ASSEMBLY FOR THE NEEDLE OF A SYRINGE BODY

(75) Inventors: Andreas Geiger, Bünde (DE); Erhard Stohlmann, Bünde (DE); Manfred Theiling, Bünde (DE)

(73) Assignee: Bunder Glas GmbH, Bunde (DE)

( * ) Notice: Subject to any disclaimer, the term of this patent is extended or adjusted under 35 U.S.C. 154(b) by 488 days.

(21) Appl. No.: 09/684,246

(22) Filed: Oct. 6, 2000

(30) Foreign Application Priority Data

Oct. 6, 1999 (DE) .......................................... 199 47 998

(51) Int. Cl.$^7$ ................................................ A61M 5/32

(52) U.S. Cl. ........................ 604/198; 604/197; 604/263; 128/919

(58) Field of Search ................................. 604/181, 182, 604/186, 187, 188, 192, 197, 198, 207, 208, 214, 218, 219, 225, 226, 227, 171, 228, 110, 263; 128/919

(56) References Cited

U.S. PATENT DOCUMENTS

| 4,333,458 A | * | 6/1982 | Margulies et al. .......... 604/220 |
| 5,259,841 A | * | 11/1993 | Hohendorf et al. ......... 604/110 |
| 5,713,871 A | * | 2/1998 | Stock ......................... 604/192 |

* cited by examiner

*Primary Examiner*—LoAn H. Thanh
(74) *Attorney, Agent, or Firm*—Laurence A. Greenberg; Werner H. Stemer; Ralph E. Locher

(57) ABSTRACT

The invention relates to a needle guard assembly for the needle part of a syringe body in the form of a needle guard that covers the needle and which is displaceable on the syringe body in the longitudinal direction, and with a grip plate being integrally formed on that end of the syringe body remote from the needle. The needle guard assembly includes a syringe body ending with a needle. A piston rod in the syringe body has a receiving part and a push-in part that telescopes into the receiving part. A syringe-body grip plate is integrally formed on the syringe body. The syringe-body grip plate opposes the needle. A needle guard is arranged longitudinally along the syringe body and covers the needle when the needle guard is displaced longitudinally.

13 Claims, 4 Drawing Sheets

NEEDLE GUARD ASSEMBLY FOR THE NEEDLE OF A SYRINGE BODY

BACKGROUND OF THE INVENTION

1. Field of the Invention

The invention relates to a needle guard assembly for the needle part of a syringe body in the form of a needle guard that covers the needle and which is displaceable on the syringe body in the longitudinal direction, and with a grip plate being integrally formed on that end of the syringe body remote from the needle.

2. Description of the Related Art

Published European Patent Application EP 0 734 738 A2 discloses a safety syringe with a safety shield. In this known syringe, the safety shield is held securely in the retracted position by projections that issue from a collar. It is only when the safety shield is turned on the syringe barrel in such a way that the projections are flush with recesses in the collar, that the safety shield can be displaced toward the needle tip. In the safety position, the safety shield is held securely by locking teeth that engage with a locking wall of the collar.

SUMMARY OF THE INVENTION

The object of the invention is to construct a needle guard for the needle part of a syringe body, such that the protective safety cap can assume the functional position simply by displacing the piston rod, without additional measures.

With the foregoing and other objects in view, there is provided, in accordance with the invention, a needle guard assembly. The needle guard assembly includes a syringe body ending with a needle. A piston rod in the syringe body has a receiving part and a push-in part that telescopes into the receiving part. A syringe-body grip plate is integrally formed on the syringe body. The syringe-body grip plate opposes the needle. A needle guard is arranged longitudinally along the syringe body and covers the needle when the needle guard is displaced longitudinally.

In accordance with another feature of the invention, the needle guard assembly further includes a catch mounting connecting the receiving part and the push-in part. The catch mounting can have a predetermined break point.

In accordance with another feature of the invention, the push-in part has a free end. A piston-rod grip plate connects to the free end.

In accordance with another feature of the invention, the syringe-body grip plate has an annular seat. The annular seat has an annular-seat diameter and the piston-rod grip plate has a piston-rod-grip-plate diameter. The annular-seat diameter can be greater than the piston-rod-grip-plate diameter.

In accordance with another feature of the invention, the annular seat can have an annular-seat end face. The piston-rod grip plate can lie flush with the annular-seat end face when the piston rod is in an inwardly telescoped state.

In accordance with another feature of the invention, the receiving part includes a longitudinally extending locking groove. The push-in part includes a longitudinally extending rib. The longitudinally extending rib matches the longitudinally extending locking groove. Alternatively, the receiving part includes a longitudinally extending rib and the push-in part includes a longitudinally extending locking groove; the longitudinally extending rib matches the longitudinally extending locking groove.

In accordance with another feature of the invention, the piston-rod grip plate includes a piston-rod-grip-plate inside and the needle guard includes a needle-guard end face. The piston-rod-grip-plate inside moves to abut the needle-guard end face.

In accordance with another feature of the invention, the needle guard includes a barb. The barb abuts the syringe-body grip plate when the needle guard is in a displaced position. The barb can attach circumferentially around the needle guard.

In accordance with another feature of the invention, the needle guard includes two opposing longitudinally extending recesses. The syringe-body grip plate can include two arc-shaped recesses. These areas complement the arc-shaped recesses.

The invention achieves this object by telescoping the piston rod parts into one another. The two parts of the piston connect to each other by a catch mounting. In one embodiment of the invention, the catch mounting has a predetermined break point. The push-in part of the piston rod can be provided at the free end with a piston rod grip plate. In a preferred embodiment, the grip plate of the syringe body has an annular seat which is perpendicular to the outside of the grip plate and whose diameter is greater than the diameter of the piston rod grip plate. In a preferred embodiment, the piston rod grip plate lies almost flush with the inner edge of the annular seat and flush with the end face of the annular seat of the grip plate of the syringe body when the piston rod is in the inwardly telescoped state.

The receiving part of the piston rod can be provided with at least one longitudinally extending locking groove. The push-in part of the piston rod can be provided with at least one longitudinally extending rib. The longitudinally extending ribs match the longitudinally extending locking grooves. According to the invention, the inside of the piston rod grip plate abuts the end face of the needle guard. A barb that is expediently arranged about the circumference at the outer end advantageously limits the displacement travel of the needle guard. The barb bears on the grip plate of the syringe body when the needle guard is in the displaced position.

In a further embodiment of the invention, the needle guard is guided securely on the syringe body. For this purpose, the grip plate of the syringe body has two arc-shaped recesses. The needle guard has two opposing longitudinally extending recesses. The needle guard is forcibly guided with the areas lying between the recesses in the arc-shaped recesses.

Other features that are considered as characteristic for the invention are set forth in the appended claims.

Although the invention is illustrated and described herein as embodied in a needle guard for the needle part of a syringe body, it is nevertheless not intended to be limited to the details shown, because various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
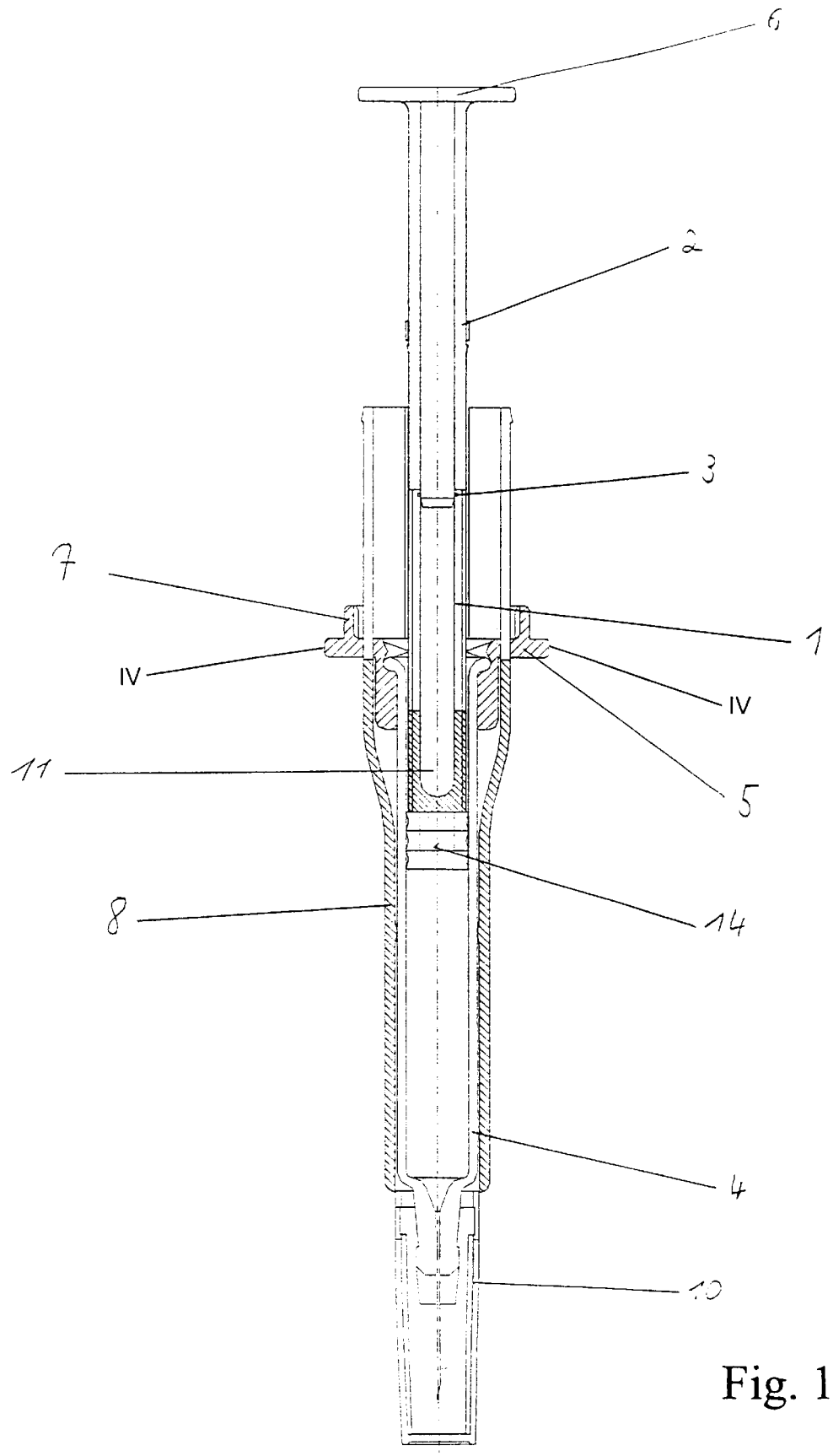
FIG. 1 is a diagrammatic, sectional view of a syringe body with a protective cap and with a displaceable needle guard in the starting position of the piston rod according to the invention.

A piston rod 1; 2 is in two parts. The parts connect to each other by a catch mounting 3. The catch mounting 3 has a predetermined break point. The piston rod has a receiving part 1 into which a part 2 of smaller diameter can be pushed telescopically. The push-in part 2 of the piston rod has a piston rod grip plate 6 at a free end. A grip plate 5 of a syringe body 4 has an annular seat 7. The annular seat 7 is perpendicular to the outside of the grip plate 5 and has a diameter greater than a diameter of the piston rod grip plate 6. As can be seen from FIG. 3, the piston rod grip plate 6 is flush with the end face of the annular seat 7 of the grip plate 5 of the syringe body 4 when the piston rod 1; 2 is in the inwardly telescoped position.

The receiving part 1 of the piston rod has two longitudinally extending locking grooves. The push-in part 2 of the piston rod has two longitudinally extending ribs that match the longitudinally extending locking grooves.

Figure 2:
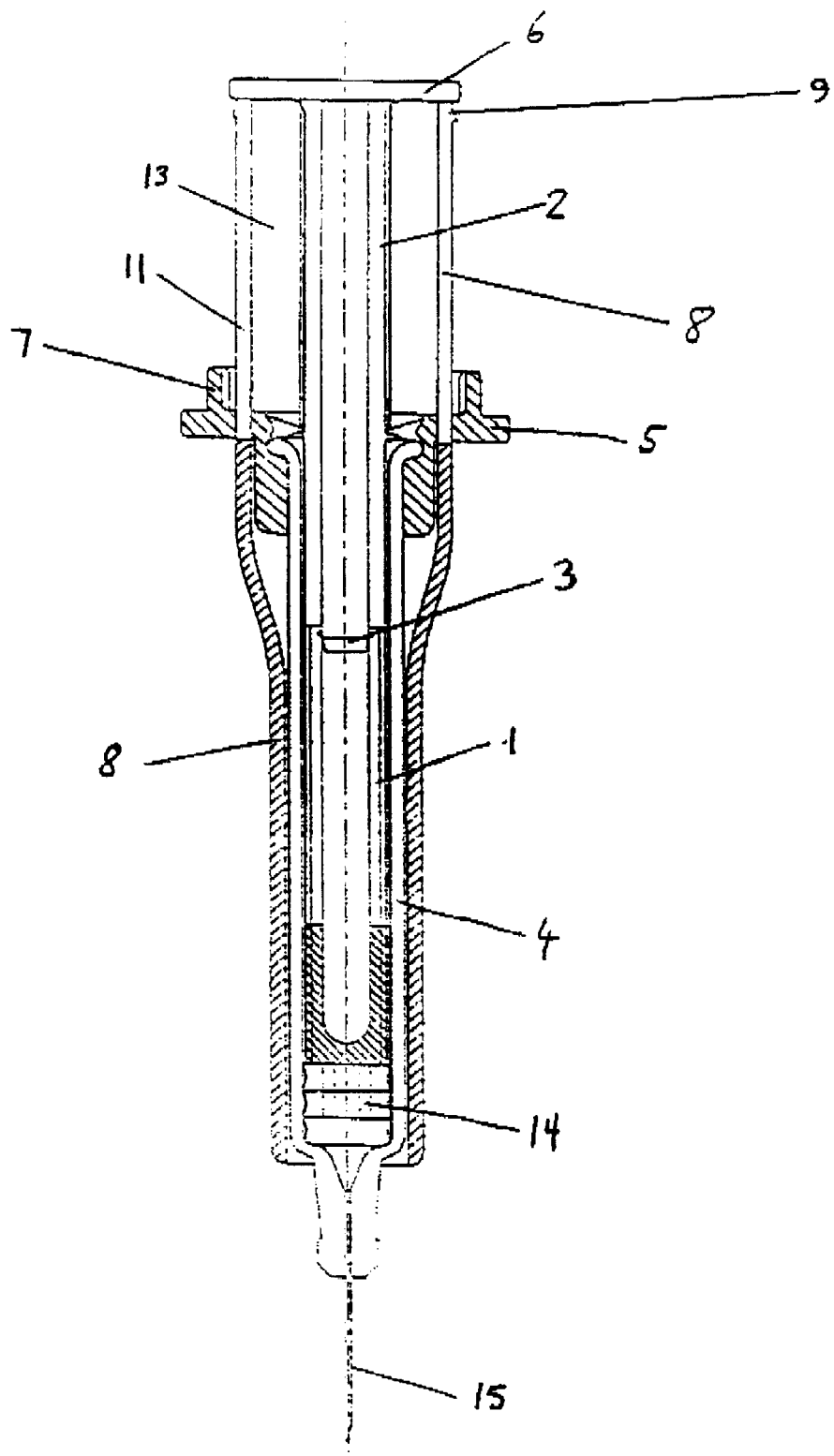
FIG. 2 is a sectional view of the syringe body with a displaced piston rod.
Figure 3:
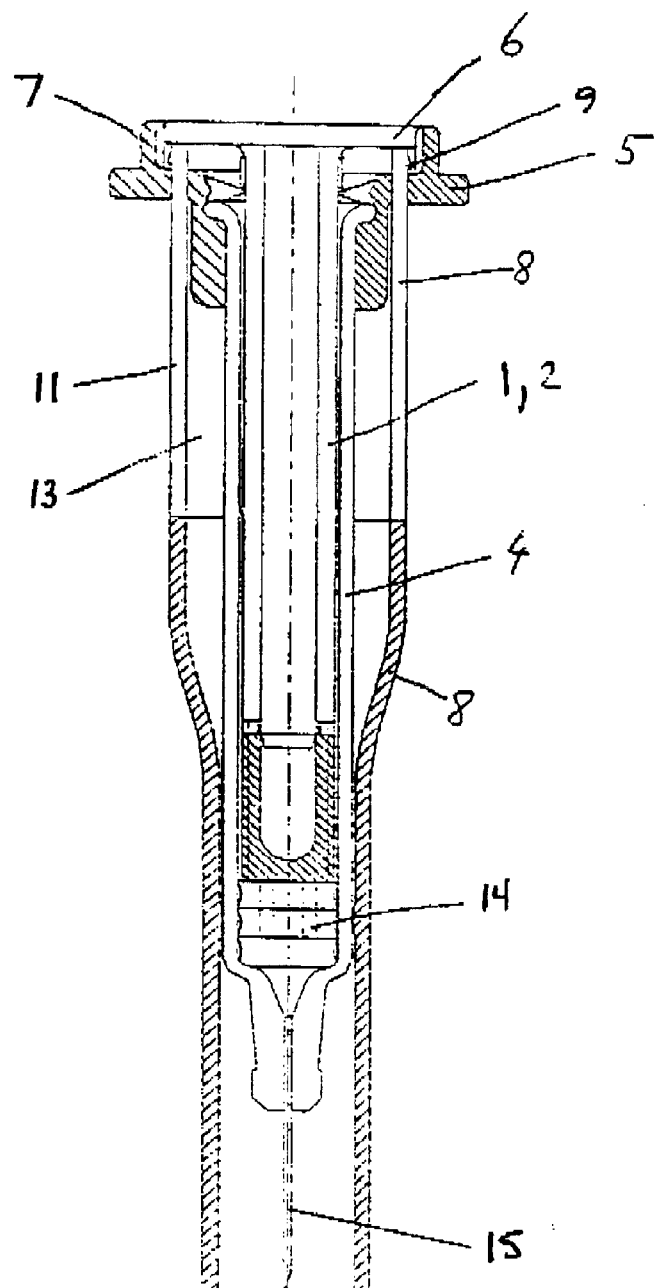
FIG. 3 is a sectional view of the syringe body with inwardly telescoped piston rod and displaced needle guard in the operative position.
Figure 4:
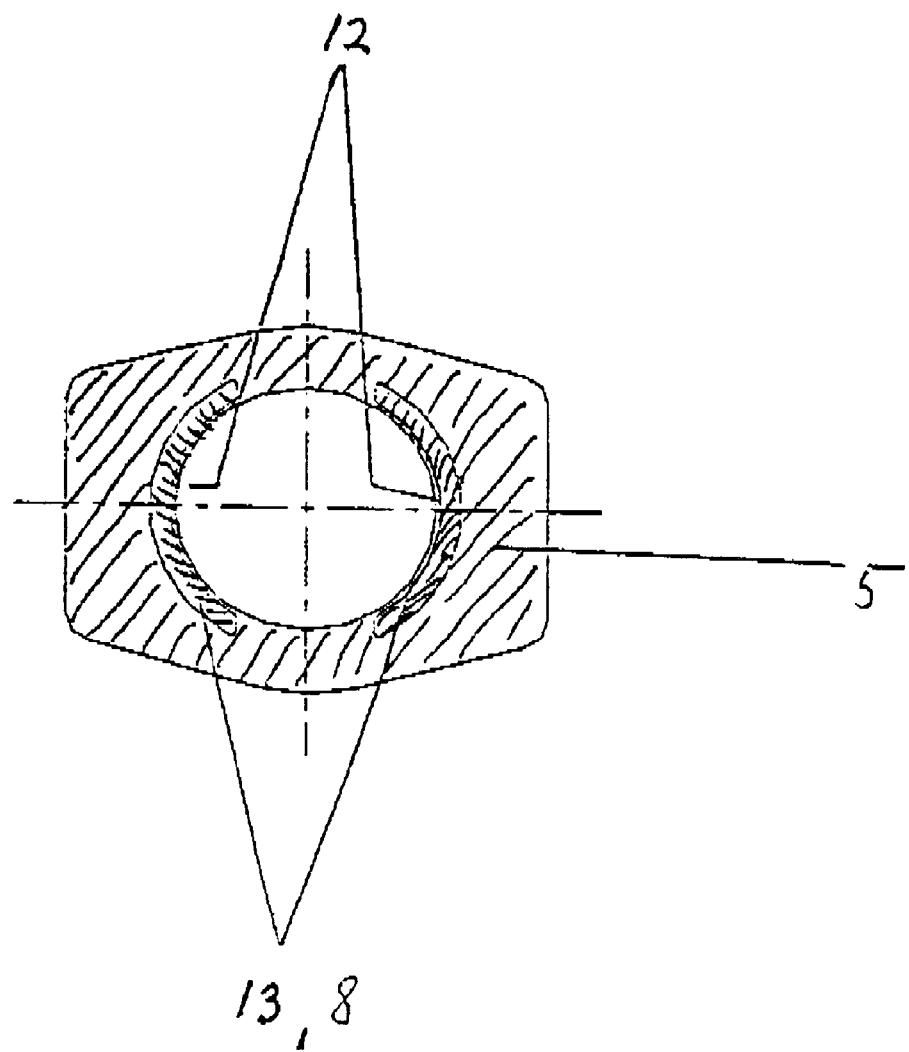
FIG. 4 is a cross sectional view taken along the line IV in FIG. 1.

The inside of the piston rod grip plate 6 abuts the end face of a needle guard 8; see FIG. 2. In this position, the piston rod rubber 14 bears on the end of the syringe body 4, i.e. the injection is complete up to this stage, the two-part piston 1; 2 acts as a unit. Upon further pressure on the piston rod grip plate 6, the catch mounting 3 between the two parts of the piston rod 1; 2 is broken and the piston rod parts telescope one into the other. Because the piston rod grip plate 6 bears on the end face of the needle guard 8, the needle guard 8 is entrained upon further insertion of the piston rod 2. Thus, in a single maneuver, the needle guard 8 covers the stuck-in needle 15. This position is shown in FIG. 3. A circumferential barb 9 limits the displacement of the needle guard 8. This barb 9 bears on the grip plate 5 of the syringe body 4 when the needle guard 8 is in the displaced position.

The needle guard 8 has two longitudinally extending recesses 11 lying opposite each other. The grip plate 5 of the syringe body 4 has two arc-shaped recesses 12. The needle guard 8 is guided forcibly with the areas 13 lying between the recesses 11 in the arc-shaped recesses 12. The known protective cap is designated by 10.

We claim:

1. A needle guard assembly comprising:
   a syringe body ending with a needle;
   a piston rod disposed in said syringe body and having a receiving part and a push-in part that telescopes into said receiving part;
   a catch mounting connecting said receiving part and said push-in part;
   a syringe-body grip plate integrally formed on said syringe body, said syringe-body grip plate opposing said needle; and
   a needle guard disposed longitudinally along said syringe body and covering said needle when said needle guard is displaced longitudinally.

2. The needle guard assembly according to claim 1, wherein said syringe-body grip plate has an annular seat.

3. The needle guard assembly according to claim 2, further comprising:
   a piston-rod grip plate having a piston-rod-grip-plate diameter; and
   said annular seat having an annular-seat diameter piston-rod-grip-plate diameter.

4. The needle guard assembly according to claim 2, further comprising:
   a piston-rod grip plate; and
   said annular seat having an annular-seat end face, and said piston-rod grip plate lying flush with said annular-seat end face when said piston rod is in an inwardly telescoped state.

5. The needle guard assembly according to claim 1, wherein said catch mounting has a predetermined break point.

6. The needle guard assembly according to claim 1, wherein said push-in part has a free end and a piston-rod grip plate connected to said free end.

7. The needle guard assembly according to claim 1, further comprising:
   a piston-rod grip plate including a piston-rod-grip-plate inside, said needle guard including a needle-guard end face, said piston-rod-grip-plate inside moving to abut said needle-guard end face.

8. A needle guard assembly comprising:
   a syringe body ending with a needle;
   a piston rod disposed in said syringe body and having a receiving part and a push-in part telescoping into said receiving part;
   a syringe-body grip plate integrally formed on said syringe body, said syringe-body grip plate opposing said needle; and
   a needle guard including a barb, said needle guard disposed longitudinally along said syringe body and covering said needle when said needle guard is displaced longitudinally.

9. The needle guard assembly according to claim 8, wherein said barb abuts said syringe-body grip plate when said needle guard is in a displaced position.

10. The needle guard assembly according to claim 8, wherein said barb attaches circumferentially around said needle guard.

11. The needle guard assembly according to claims 1, wherein said needle guard includes two opposing longitudinally extending recesses.

12. The needle guard assembly according to claim 1, wherein said syringe-body grip plate includes two arc-shaped recesses.

13. The needle guard assembly according to claim 1, wherein said needle guard has two opposing longitudinally extending recesses formed therein and two areas lying between said recesses, and said syringe-body grip plate has two arc-shaped recesses formed therein, said areas complementing the arc-shaped recesses.

\* \* \* \* \*